United States Patent [19]

Mödinger

[11] Patent Number: 5,179,282
[45] Date of Patent: Jan. 12, 1993

[54] METHOD FOR ASCERTAINING THE CONTENT OF AN INGREDIENT OF FLUX IN AUTOMATIC SOLDERING MACHINES

[76] Inventor: Volker Mödinger, Kirschblütenweg 11, D-7000 Stuttgart 80, Fed. Rep. of Germany

[21] Appl. No.: 799,838

[22] Filed: Nov. 29, 1991

[30] Foreign Application Priority Data

Nov. 30, 1990 [DE] Fed. Rep. of Germany ....... 4038255

[51] Int. Cl.$^5$ .............................................. G01N 21/31
[52] U.S. Cl. .................................. 250/343; 250/373; 228/8; 228/56.5
[58] Field of Search ................. 228/8, 104, 56.2, 56.5; 250/343, 341, 373

[56] References Cited

U.S. PATENT DOCUMENTS 4,792,078 12/1988 Takahashi ............................. 228/8
4,890,781 1/1990 Johnson et al. ......................... 228/8

Primary Examiner—Carolyn E. Fields
Attorney, Agent, or Firm—Edwin E. Greigg; Ronald E. Greigg

[57] ABSTRACT

A method and apparatus for ascertaining the content of an ingredient of flux in automatic soldering machines, in which the attenuation or transmission of electromagnetic radiation by the flux is measured, and the content of this ingredient is ascertained by comparison of the measured value with known values, stored in memory, wherein to avoid contamination of the measured flux and the production of new waste substances, the attenuation or transmission is measured in a frequency range in which a strong attenuation by the ingredient to be determined occurs; and moreover a comparison measurement of a reference medium is performed at the same frequency; and finally, the difference between the two measured values is used for comparison with the known values stored in memory.

25 Claims, 1 Drawing Sheet

METHOD FOR ASCERTAINING THE CONTENT OF AN INGREDIENT OF FLUX IN AUTOMATIC SOLDERING MACHINES

BACKGROUND OF THE INVENTION

The invention is based on a method for ascertaining the content of an ingredient of flux in automatic soldering machines as defined hereinafter.

Electronic components are soldered onto printed circuit boards in automatic soldering machines; the surfaces to be soldered have to be moistened first with a flux. Fluxes of this kind comprise solid or active ingredients such as colophon, organic salts and acids, on the one hand, and a thinner in the form of organic solvents with a certain proportion of water, on the other. Only when the flux composition is constant can uniform soldering results be assured. This requires monitoring the content of the various ingredients of the flux used and correcting it as needed by adding thinner or by replacing the flux. A change in the content of the various ingredients occurs especially because, first, the volatile solvents evaporate during soldering, thereby increasing the concentration of solid or active ingredients in the flux, and second, the solvents used are highly hygroscopic, so that the water content increases with time.

In the laboratory, determining the content of the various ingredients of flux can be done without any particular difficulty; but with a soldering machine in operation, making such a determination so as to assure an always-constant flux composition is too time-consuming. Adjusting the constant flux composition therefore requires fast measurement during soldering machine operation. In known methods for determining the solid or active ingredient content in flux during the operation of an automatic soldering machine (German patent disclosure documents DE-OS 37 37 564 and DE-OS 35 37 368), photometric titration is performed for this purpose. In this process, some of the flux is withdrawn from the automatic soldering machine, and the transparency of the sample is measured as a function of the addition of a process fluid. These methods have the disadvantage, however, that the flux required for the measurement cannot be used as flux later because process fluid will have been added, and so it has to be disposed of as a waste product, and that the measuring instrument for measuring the added quantity of process fluid is complicated in structure and vulnerable to malfunction. For this reason, to assure good soldering results, it is often typically done to simply replace the flux in the automatic soldering machine completely and dispose of it at regular time intervals, such as once a week, without checking these ingredients.

OBJECT AND SUMMARY OF THE INVENTION

The method according to the invention has the advantage that the solid or active ingredient content and/or the water content of flux in automatic soldering machines can be ascertained during soldering machine operation without destroying the flux and without producing new waste products, and that from the results obtained, the flux composition can be adjusted to assure uniform soldering outcomes.

Measuring the attenuation or transmission in a frequency range in which the ingredient to be determined causes a pronounced attenuation makes the attenuation strong enough that reliable and evaluatable measurement findings can be made. The comparative measurement of a reference medium at the same frequency effectively eliminates external influences, such as the proportion of the attenuation not caused by the ingredient to be determined, or a change in radiation intensity caused by aging of a lamp. The difference in the measured values between the primary measurement and the comparison measurement is then compared with previously determined values, stored in memory, for known proportions of the various ingredients, and the proportion of this ingredient in the sample quantity is determined from that. In a feature of the invention, both measurements are done at the same temperature, which advantageously precludes adulteration of the results from temperature-dependent factors.

To determine the water content of flux, in a further feature of the invention the two measurements are performed in the infrared frequency range, and air is used as the reference medium. The infrared frequency range has proved to be particularly suitable, because water exhibits strong absorption bands in this range.

In a further feature of the invention, the determination of the solid or active ingredient content is made in the frequency range between ultraviolet and far infrared, preferably in the far infrared, because the solids or active ingredients used in the flux exhibit strong absorption bands in this range. Thinner, that is, solvent with a proportion of water or in other words flux without any active ingredient, is used as the reference medium.

In a further development of these characteristics, the measurements for determining a plurality of solids or active ingredients in the flux are performed at a frequency in which there is strong attenuation by a solid or active ingredient that can be considered the primary ingredient. This simplifies the measuring method and makes it faster and less expensive.

In another feature of the invention, in a first method step, an attenuation or transmission measurement is performed at a frequency of strong attenuation by the solid or active ingredient in the thinner, as the reference medium, used in the flux; in a second method step, an attenuation or transmission measurement is performed at a frequency of strong attenuation by water in air as the reference medium; and as the third method step, an attenuation or transmission measurement in the flux is performed at both the above two frequencies, simultaneously. The values found in the measurements of the flux are each subtracted from the measured values of the comparison measurements, and the results are each compared with the values previously ascertained and stored in memory for the known solid or active ingredient content or the known water content, respectively. This kind of method procedure speeds up the overall method and simplifies it and reduces the costs for a measuring instrument to perform the method. Naturally, the order of measurements can be transposed; for instance, the two simultaneous measurements of the flux may be performed first and then the two comparison measurements. The decisive factor is that the two measurements of the flux be performed simultaneously.

In a further feature of the invention, in addition to the extinction or transmission measurements the density and temperature of the flux are measured; the density is standardized to a predetermined temperature; and finally, the standardized density is corrected by the water content of the flux. This embodiment has the advantage that in cases in which the solid or active ingredient content can be ascertained only with difficulty by attenuation measurement, it is possible to calculate the solid or active ingredient content from the density and water content of the flux. To this end, the density is first standardized to a predetermined temperature and then corrected by the water content of the flux. The resultant density of the flux is compared with known values for a predetermined solid or active ingredient content of the flux. The water content can in particular be ascertained, in accordance with the method of the invention, by attenuation or transmission measurement.

This embodiment may advantageously also be used to determine the content of contaminants in the flux. To this end, the temperature-standardized density, corrected by the water content, is compared with the density resulting from the measured solid or active ingredient content. The degree of contamination can then be calculated from the difference between the two values.

In a further feature of the invention, the flux is filtered prior to the attenuation or transmission measurement. Thus contaminants can advantageously be kept out of the measurement sample, in order to prevent adulteration of the outcome of measurement.

In a further feature of the invention, the ascertained values of the contents of the flux are used for automatically adjusting the flux composition; depending on the ascertained solid or active ingredient content, a thinner is added to the flux, and depending on the ascertained water content, the flux is replaced, either entirely or in part, with new flux. If an increase in the solid or active ingredient content is ascertained, then a suitable quantity of thinner is added to the flux so that this content matches the set-point value. Accordingly, replacing some of the flux with new flux can compensate for an overly high proportion of water ascertained in the flux.

The apparatus according to the invention for performing the method has two radiolucent sample vessels, each of which is assigned a radiation source and a detector; the two sample vessels are connected to one another by flux lines and are connected to supply containers for flux and thinner, and a density measuring instrument, a temperature measuring instrument and a pump are present in the flux lines. By means of this apparatus, all the necessary measurements can advantageously be performed quickly and simply. To this end, thinner is first pumped into the sample vessel, and a comparison measurement at the attenuation frequency of the solid or active ingredient is performed in one sample vessel. Then the thinner is pumped back out of the sample vessels and the comparison measurement is then made at the attenuation frequency of water in the other, now-empty, sample vessel. Finally, flux is pumped into both sample vessels, and a measurement at the attenuation frequency of the solid or active ingredient is performed in one sample vessel and simultaneously a measurement at the attenuation frequency of water is performed in the other sample vessel. The measured values are each delivered to a computer and compared with the values stored in memory. The contents of ingredients found thereby are used to adjust the composition of the flux. To this end, the computer controls one pump with which thinner can be pumped into the flux and a second pump for delivering new flux to the fluxer.

The invention will be better understood and further objects and advantages thereof will become more apparent from the ensuing detailed description of a preferred embodiment taken in conjunction with the drawing.

BRIEF DESCRIPTION OF THE DRAWING

The single figure of the drawing shows the disposition of the apparatus according to the invention in a schematic view.

DESCRIPTION OF THE PREFERRED EMBODIMENT

Figure 1:
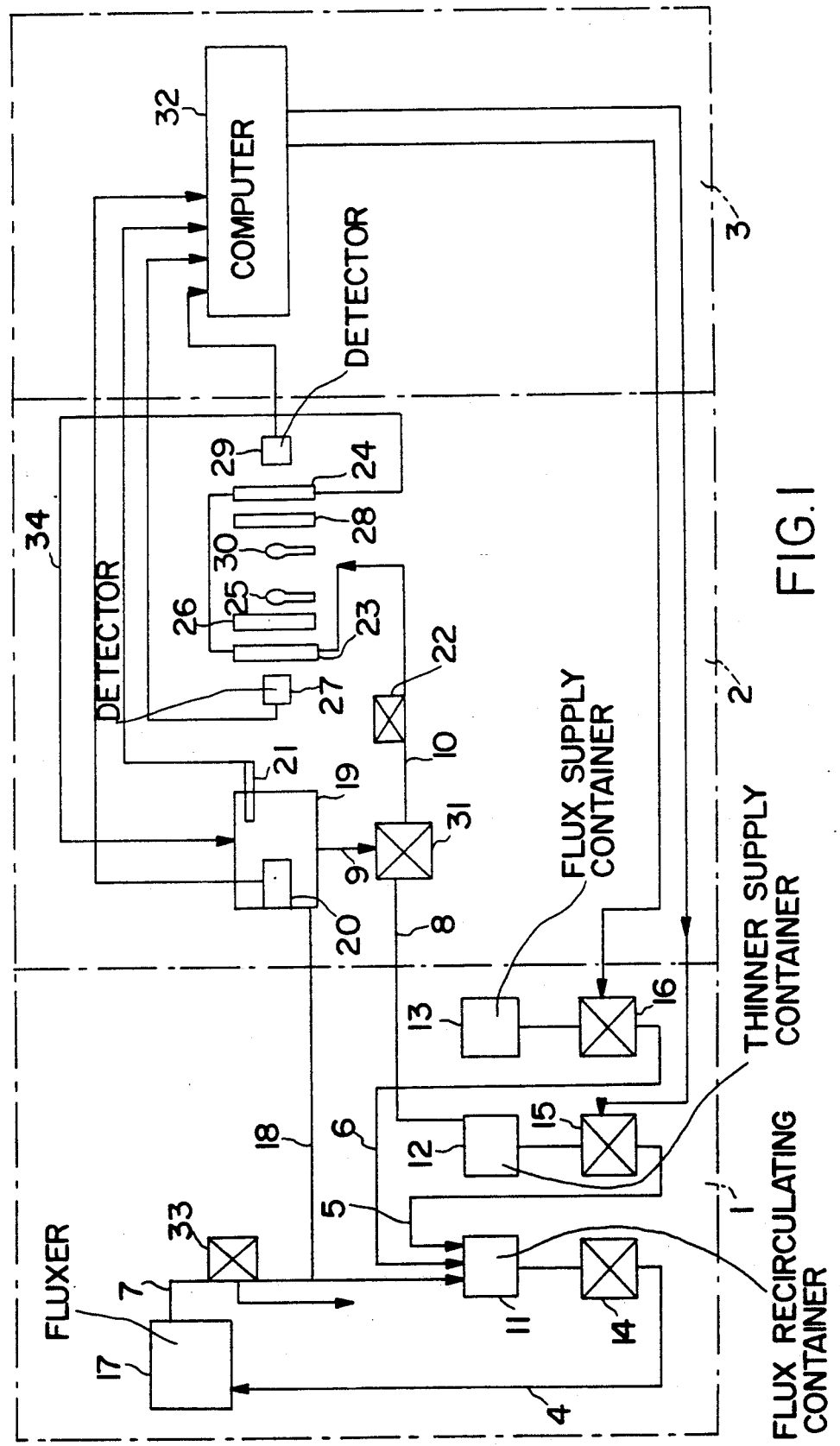

The apparatus shown is made up of three parts, namely the soldering machine region 1, the measuring region 2 and the evaluation region 3. In the soldering machine region 1, a fluxer 17 is connected, via a pump 14 located in a flux line 4, to a flux recirculating container 11 which in turn is connected on its other end to the fluxer, via a 3/2-way valve 33 present in a flux line 7. Connected to the other end of the 3/2-way valve is a disposal line, for removal of flux that is to be exchanged from the flux loop. The flux recirculating container 11 also communicates with a thinner supply container 12, via a flux line 5 in which a pump 15 is disposed, and with a flux supply container 13 via a flux line 6, in which a pump 16 is disposed. From the flux line 7, a bypass line 18 branches off to a density measuring container 19, which contains a density measuring instrument 20 and a temperature sensor 21.

The thinner supply container 12 and the density measuring container 19 communicate with two laboratory cells 23 and 24, connected in series with one another, via flux lines 8 and 9, respectively, a 3/2-way valve 31, and a common flux line 10, a pump 22 being provided in the latter flux line. From the second laboratory dish 24, a return line 34 leads back to the density measuring container 19. Each of the laboratory cells 23 and 24 is assigned a respective light source 25 and 30, filter 26 and 28, and detector 27 and 29, which are connected to a computer 32. The temperature sensor 21 and the density measuring instrument 20 are also connected to the computer 32. From the computer 32, control lines also lead to the pumps 15 and 16.

With the pump 14, the flux is recirculated continuously to the fluxer 17 from the recirculating container 11. Via the bypass line 18, flux is supplied to the density measuring container 19, in which the density and temperature are ascertained by means of the density measuring instrument 20 and temperature sensor 21, respectively, and a measure of the density and temperature are passed on to the computer 32. Via the valve 31, the pump 22 alternatingly supplies thinner and flux through the cells 23 and 24 and then empties the cells again.

The light emitted by the light source 25 is made monochromatic by the filter 26; it shines through the cell 23 and a value of the transmitted light is detected by the detector 27. The measured values for an empty and a flux-filled cell are passed on by the detector 27 to the computer 32, where they are evaluated. The light emitted by the light source 30 is made monochromatic by the filter 28; it shines through the cell 24 and a value of the transmitted light is detected by the detector 29. The measured values of flux and thinner are again passed on by the detector 29 to the computer 32 and evaluated there. Higher measured attenuation values represent higher proportions of water or solid/active ingredient.

Depending on the evaluated findings, the computer controls the pump 15 to reduce the solid or active ingredient content by adding thinner from the supply container 12 and the pump 16 to pump new flux from the supply container 13 to reduce the water content, once some of the flux having an overly high water content has first been removed from the flux loop via the valve 33.

By comparing the density of the flux, measured in the density measuring instrument 20, with the density found from the measured water and solid/active ingredient content, the degree of contamination is calculated, and if necessary all or some of the flux is replaced with new flux.

All the characteristics described herein, recited in the following claims and shown in the drawing may be essential to the invention either singly or in any arbitrary combination with one another.

The foregoing relates to a preferred exemplary embodiment of the invention, it being understood that other variants and embodiments thereof are possible within the spirit and scope of the invention, the latter being defined by the appended claims.

What is claimed and desired to be secured by Letters Patent of the United States is:

1. A method for ascertaining the content of an ingredient of flux in automatic soldering machines, which comprises measuring an attenuation or transmission of electromagnetic radiation by the flux, ascertaining the content of this ingredient by comparison of the measured value with known values stored in memory in a computer, measuring the attenuation or transmission in a frequency range in which a strong attenuation by the ingredient to be determined occurs, comparing a measurement of a reference medium at the same frequency; and comparing the difference between the two measured values for comparison with the known values stored in memory.

2. A method as defined by claim 1, in which the two measurements are performed at the same temperature.

3. A method as defined by claim 2, in which the two measurements are performed in the infrared frequency range, at a frequency of strong attenuation by water, and that air is used as the reference medium.

4. A method as defined by claim 2, in which the measurements are performed in the frequency range between ultraviolet and far infrared, at a frequency of strong attenuation by the solid or active ingredient of the flux, and that the thinner used in the flux is used as the reference medium.

5. A method as defined by claim 4, in which the measurements are performed at a frequency of strong attenuation by one of a plurality of solid or active ingredients of the flux, which ingredient is to be considered primary.

6. A method as defined by claim 2, in which an attenuation or transmission measurement is performed at a frequency of strong extinction by the solid or active ingredient in the thinner, as the reference medium, used in the flux; that in a second method step, an attenuation or transmission measurement is performed at a frequency of strong attenuation by water, in air as the reference medium; that as the third method step, attenuation or transmission measurements in the flux are performed at both the above two frequencies, simultaneously; and that finally, the difference between the two last-mentioned measured values and the measured values of the applicable comparison measurement are each used for comparison with values previously ascertained and stored in memory.

7. A method as defined by claim 2, in which additionally the density and temperature of the flux are measured; that the density is standardized to a predetermined temperature; and that finally, the standardized density is corrected by the water content of the flux.

8. A method as defined by claim 1, in which the two measurements are performed in the infrared frequency range, at a frequency of strong attenuation by water, and that air is used as the reference medium.

9. A method, as defined by claim 8, in which an attenuation or transmission measurement is performed at a frequency of strong extinction by the solid or active ingredient in the thinner, as the reference medium, used in the flux; that in a second method step, an attenuation or transmission measurement is performed at a frequency of strong attenuation by water, in air as the reference medium; that as the third method step, attenuation or transmission measurements in the flux are performed at both the above two frequencies, simultaneously; and that finally, the difference between the two last-mentioned measured values and the measured values of the applicable comparison measurement are each used for comparison with values previously ascertained and stored in memory.

10. A method as defined by claim 8, in which additionally the density and temperature of the flux are measured; that the density is standardized to a predetermined temperature; and that finally, the standardized density is corrected by the water content of the flux.

11. A method as defined by claim 1, in which the measurements are performed in the frequency range between ultraviolet and far infrared, at a frequency of strong attenuation by the solid or active ingredient of the flux, and that the thinner used in the flux is used as the reference medium.

12. A method as defined by claim 11, in which the measurements are performed at a frequency of strong attenuation by one of a plurality of solid or active ingredients of the flux, which ingredient is to be considered primary.

13. A method, as defined by claim 12, in which an attenuation or transmission measurement is performed at a frequency of strong extinction by the solid or active ingredient in the thinner, as the reference medium, used in the flux; that in a second method step, an attenuation or transmission measurement is performed at a frequency of strong attenuation by water, in air as the reference medium; that as the third method step, attenuation or transmission measurements in the flux are performed at both the above two frequencies, simultaneously; and that finally, the difference between the two last-mentioned measured values and the measured values of the applicable comparison measurement are each used for comparison with values previously ascertained and stored in memory.

14. A method as defined by claim 12, in which additionally the density and temperature of the flux are measured; that the density is standardized to a predetermined temperature; and that finally, the standardized density is corrected by the water content of the flux.

15. A method as defined by claim 11, in which an attenuation or transmission measurement is performed at a frequency of strong extinction by the solid or active ingredient in the thinner, as the reference medium, used in the flux; that in a second method step, an attenuation or transmission measurement is performed at a frequency of strong attenuation by water, in air as the reference medium; that as the third method step, attenuation or transmission measurements in the flux are performed at both the above two frequencies, simultaneously; and that finally, the difference between the two last-mentioned measured values and the measured values of the applicable comparison measurement are each used for comparison with values previously ascertained and stored in memory.

16. A method as defined by claim 11, in which additionally the density and temperature of the flux are measured; that the density is standardized to a predetermined temperature; and that finally, the standardized density is corrected by the water content of the flux.

17. A method, as defined by claim 1, in which an attenuation or transmission measurement is performed at a frequency of strong extinction by the solid or active ingredient in the thinner, as the reference medium, used in the flux; that in a second method step, an attenuation or transmission measurement is performed at a frequency of strong attenuation by water, in air as the reference medium; that as the third method step, attenuation or transmission measurements in the flux are performed at both the above two frequencies, simultaneously; and that finally, the difference between the two last-mentioned measured values and the measured values of the applicable comparison measurement are each used for comparison with values previously ascertained and stored in memory.

18. A method as defined by claim 17, in which additionally the density and temperature of the flux are measured; that the density is standardized to a predetermined temperature; and that finally, the standardized density is corrected by the water content of the flux.

19. A method as defined by claim 11, in which additionally the density and temperature of the flux are measured; that the density is standardized to a predetermined temperature; and that finally, the standardized density is corrected by the water content of the flux.

20. A method as defined by claim 19, in which the solid/active ingredient content of the flux is determined from the corrected density and the water content.

21. A method as defined by claim 19, in which the degree of contamination of the flux is determined from the corrected density, the water content, and the solid/active ingredient content ascertained by an attenuation measurement.

22. A method as defined by claim 1, in which the flux is filtered prior to the attenuation or transmission measurement.

23. A method as defined by claim 1, in which the ascertained values of the ingredients of the flux are used for automatically adjusting the flux composition, in that thinner is added to the flux depending on the ascertained solid or active ingredient content, and the flux is replaced entirely or in part with new flux depending on the ascertained water content.

24. An apparatus for ascertaining a content of an ingredient of flux in an automatic soldering machine which comprises a soldering machine region (1), a measuring region (2), and an evaluation region (3), the soldering region includes a flux supply container (13), a first pump (16) in a first flux line (6) from said flux supply container to a flux recirculating container (11), a thinner supply container (12), a second pump (15) in a second flux line (5) from said thinner-supply container (12) to said flux recirculating container (11), a fluxer (17), a third pump in a third flux line (4) from said flux recirculating container (11) to said fluxer (17), a fourth flux line (7) from said fluxer (17) to said flux recirculating container (11), said measuring region (2) includes density measuring container (19) which communicates with a bypass line (18) connected to said fourth flux line (7) between said fluxer and said flux recirculating container (11), said density measuring container (19) includes therein a density measuring instrument (20) and a temperature sensor (21), said density measuring container (19) is connected by a fifth flux line (9) with a valve (31) which is also connected with said thinner supply container (12) via a sixth flux line (8), said value (31) is connected with a fourth pump (22) which is connected with a first sample vessel (23), said first sample vessel is connected in series with a second sample vessel (24) which is turn is connected with said density measuring container (19), a first radiation source is positioned juxtaposed said first sample vessel (23) for directing radiation through said first ample vessel onto a first detector (27) which measures and records any radiation passing through said first sample vessel, a second radiation source is positioned juxtaposed said second sample vessel (24) for directing radiation through said second sample vessel onto a second detector (29) which measures and records any radiation passing through said second sample vessel, said evaluation region (3) includes a computer (32) which receives output signals from said density measuring instrument (20), said temperature sensor (21), and said first and second detectors (27 and 29), said computer evaluates the output signals and depending on the output signals directs signals to control said first and second pumps to reduce the flux mixture by adding thinner from said thinner supply container (12) to the recirculating container (11) and for pumping new flux from said supply container (13) to said flux recirculating container (11) and a valve (33) is provided in the fourth flux line (7) for removal of flux from the apparatus which contains a high water content.

25. An apparatus as set forth in claim 24 which includes a first monochromatic filter between said first radiation source and said first sample vessel, and a second monochromatic filter between said second radiation source and said second sample vessel.

* * * * *